United States Patent
Childers et al.

(10) Patent No.: US 6,306,859 B1
(45) Date of Patent: Oct. 23, 2001

(54) N-SUBSTITUTED IMIDE DERIVATIVES WITH SEROTONERGIC ACTIVITY

(75) Inventors: Wayne E. Childers, New Hope, PA (US); Michael G. Kelly, Newbury Park, CA (US); Gan Zhang, Plainsboro, NJ (US); Yvette L. Palmer, Yardley; Edward J. Podlesny, New Tripoli, both of PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/516,137

(22) Filed: Mar. 1, 2000

Related U.S. Application Data

(60) Provisional application No. 60/160,089, filed on Mar. 2, 1999, now abandoned.

(51) Int. Cl.[7] ............... A61K 31/495; A61K 31/496; C07D 295/145; C07D 403/10; C07D 405/10
(52) U.S. Cl. ............... 514/252.13; 514/253.01; 514/253.04; 514/253.05; 514/253.06; 514/254.02; 514/254.03; 514/254.06; 514/254.09; 514/254.1; 514/254.11; 514/255.03; 514/321; 514/323; 514/331; 514/357; 544/360; 544/362; 544/363; 544/364; 544/365; 544/368; 544/371; 544/373; 544/376; 544/377; 544/379; 544/393; 546/233; 546/234; 546/337; 546/197; 546/201
(58) Field of Search ................... 544/393, 373, 544/377, 360, 362–365, 368, 371, 376, 379; 514/254.09, 254.11, 255.03, 252.13, 253.04–253.06, 253.01, 254.02, 254.03, 254.1

(56) References Cited

U.S. PATENT DOCUMENTS

| | | |
|---|---|---|
| 3,717,634 | 2/1973 | Wu et al. . |
| 4,921,958 | 5/1990 | Abou-Gharbia et al. . |
| 4,988,814 | 1/1991 | Abou-Gharbia et al. . |
| 5,010,078 | 4/1991 | Abou-Gharbia et al. . |
| 5,106,849 | 4/1992 | Abou-Gharbia et al. . |
| 5,143,916 | 9/1992 | Lavielle et al. . |
| 5,162,321 | 11/1992 | Lavielle et al. . |
| 5,162,324 | 11/1992 | Lavielle et al. . |
| 5,166,156 | 11/1992 | Lavielle et al. . |
| 5,166,157 | 11/1992 | Lavielle et al. . |
| 5,240,942 | 8/1993 | Lavielle et al. . |
| 5,242,933 | 9/1993 | Lavielle et al. . |
| 5,250,544 | 10/1993 | Lavielle et al. . |
| 5,254,552 | 10/1993 | Abou-Gharbia et al. . |
| 5,260,317 | 11/1993 | Lavielle et al. . |
| 5,278,160 | 1/1994 | Abou-Gharbia et al. . |
| 5,278,185 | 1/1994 | Lavielle et al. . |
| 5,292,761 | 3/1994 | Lavielle et al. . |
| 5,340,812 | 8/1994 | Cliffe . |
| 5,364,849 | 11/1994 | Cliffe . |
| 5,380,725 | 1/1995 | Abou-Gharbia et al. . |
| 5,382,583 | 1/1995 | Cliffe . |
| 5,420,278 | 5/1995 | Cliffe . |
| 5,482,940 | 1/1996 | Abou-Gharbia et al. . |
| 5,486,518 | 1/1996 | Yardley et al. . |
| 5,541,326 | 7/1996 | Cliffe . |
| 5,696,123 | 12/1997 | Dollinger et al. . |
| 5,708,006 | 1/1998 | Dollinger et al. . |

FOREIGN PATENT DOCUMENTS

| | | |
|---|---|---|
| 19520499A1 | 3/1996 | (DE) . |
| 434561A2 | 12/1990 | (EP) . |
| 496692A1 | 7/1992 | (EP) . |
| 343961B1 | 1/1996 | (EP) . |
| 795328A1 | 9/1997 | (EP) . |
| 395312B1 | 5/1999 | (EP) . |
| 2303033A | 11/1996 | (GB) . |
| 9608480A1 | 3/1996 | (WO) . |
| 9640136A1 | 12/1996 | (WO) . |

OTHER PUBLICATIONS

J. of Pharm. & Tox. Methods 40, pp. 47–55 (1998); Dunlop, J. et al.
J. of Med. Chem., vol. 30, No1 1 pp.1–12 (Jan. 1987); Glennon, R. A.
Nippon Rinsho 47; (special edition); 1241–1248; (1989); Hisayama, T., & Takayanagi, I. (Japanese Version).
Nippon Rinsho 47 (spec. edit.) 1241–1248 (1989( Hisayama T & Takayanagi, I (English Trans).
Psychopathology vol. 22; pp. 21–26 (1989) Feighner, J.P., & Boyer, W.F.
Trends in Pharm. Sci., vol. 11, pp. 95–96; (Mar. 1990); Saxena, P.R. & Villalon, C.M.
Naurnyn–Schmiedeberg's Arch. Pharm. (1996) 354: 226–236 Zgombick, J. M. et al.
Brit. J. of Pharm., 109, pp. 1120–1127 (1993) Lazareno, S.; Birdsall, N. J. M.
Annual Reports in med. Cham. vol. 30 Ramussen, K. & Rocco, V.P.
Jpn. J. Pharmacol.. Suppl., 58, 313 (1992) N. Matsuki, et al.

*Primary Examiner*—Emily Bernhardt
(74) *Attorney, Agent, or Firm*—Rebecca R. Barrett

(57) ABSTRACT

Compounds of the Formula (I)

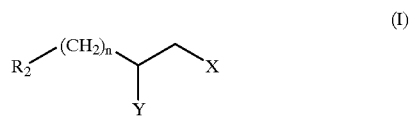

wherein $R_2$, Y, X and n are as defined in the specification which compounds are useful in the treatment of disorders associated with serotonergic neuron-related diseases.

18 Claims, No Drawings

N-SUBSTITUTED IMIDE DERIVATIVES WITH SEROTONERGIC ACTIVITY

CROSS REFERENCE TO RELATED APPLICATIONS

This application claims benefit of U.S. Provisional Application No. 60/160,089, which was converted from U.S. patent application Ser. No. 09/261,298, filed Mar. 2, 1999, now abandoned.

BACKGROUND OF THE INVENTION a) Field of the Invention

The present invention relates to a series of novel N-substituted imide derivatives and non-toxic salts thereof, which have a high affinity for the serotonin $5\text{-}HT_{1A}$ receptor, acting as partial agonists and antagonists and are useful for preventing and treating serotonergic neuron-related diseases.

b) Description of the Prior Art

It is known that serotonin [5-hydroxytryptamine (5-HT)] as a neurotransmitter has correlations with various physiological phenomena, such as appetite, memory, thermoregulation, sleep, sexual behavior, anxiety, depression and stress [Glennon, R. A., J. Med. Chem., 30, 1 (1987)].

It is also known that compounds acting on a $5\text{-}HT_{1A}$ receptor which is one of the serotonin-susceptive receptors are useful for preventing and treating anxiety, depression, eating disorders, high blood pressure and emesis. Results of studies on various compounds have been reported [see "Nippon Rinsho (Japanese Journal of Clinical Medicine)" vol. 47, special edition. pp. 1241–1248 (1989); J. P. Feighnev, W. F. Boyer, Psychopathology, 22, 21 (1989); P. R. Saxena, C. M. Villalon, TIPS, 11, 95 (1990); N. Matsuki, et al., Jpn. J. Pharmacol. Suppl., 58, 313 (1992).

Compounds having selective partial agonist activity at the $5\text{-}HT_{1A}$ receptor have established a presence in the marketplace as effective anxiolytic agents (buspirone HCl, 8-[4-[4-(2-pyrimidinyl)-1-piperazinyl]butyl]-8-azaspiro[4.5] decane-7,9-dione monohydrochloride, U.S. Pat. No. 3,717, 634). $5\text{-}HT_{1A}$ agonists and antagonists are being evaluated in the laboratory and in the clinic for use in the treatment of several diseases such as anxiety, depression, schizophrenia, the cognitive deficits resulting from neurodegenerative diseases like Alzheirner's Disease, and additionally prostate cancer (K. Rasmussen and V. P. Rocco, *Recent Progress in Serotonin* ($5\text{-}HT_{1A}$ *Receptor Modulators*, in Annual Reports in Medicinal Chemistry, Volume 30, J. A. Bristol, ed., pp. 1–9 (1995)).

A series of naphylpiperazines useful as $5\text{-}HT_{1A}$ receptor ligands having the generic structure:

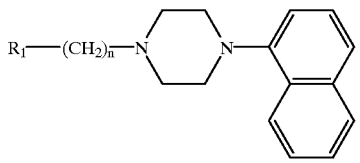

are described in EPO 434561-A2 and U.S. Pat. Nos. 5,143, 916; 5,162,321; 5,162,324; 5,166,156 and 5,166,157.

Reported in WO 9640136-A1 is a series of N-(piperidinyl or piperazinyl alkyl)phenyl acetamide derivatives as alpha 1a adrenergic receptor antagonists having the generic formula:

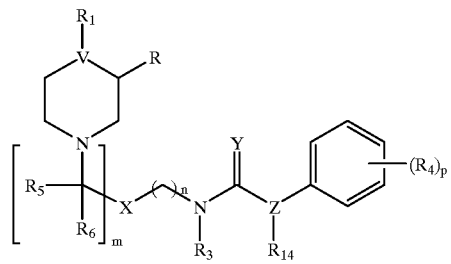

EP 795328-A1 discloses a new use for naphthalene serotonin $5\text{-}HT_{1D}$ receptor antagonists of the generic formula:

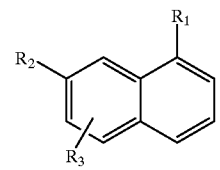

as inhibitors of cell growth in human small cell lung carcinoma, where $R_1$ is a moiety of formulae:

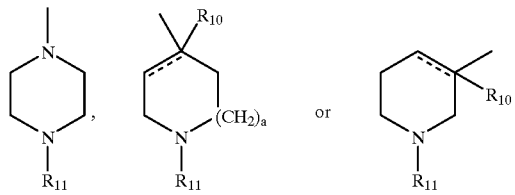

Reported in GB 2303303-A is a method of using $5HT_{1A}$ or $5HT_2$ receptor antagonists of the formulae:

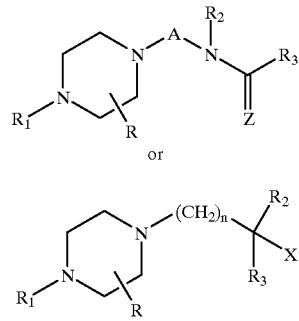

for preventing or reducing the side effects of serotonin re-uptake inhibitors

Reported in DE 19520499-A1, WO 9608480A1, and U.S. Pat. Nos. 5,696,123 and 5,708,006 is a series of aralkyl amines, amides and ureas as neurokinin antagonists.

The N-substituted imide derivatives or pharmaceutically acceptable salts thereof of the present invention and described herein are useful in the treatment of disorders associated with serotonergic neuron-related diseases such as anxiety, depression, eating disorders, high blood pressure, emesis, schizophrenia, the cognitive deficits resulting from neurodegenerative diseases of Alzheimer's Disease and additionally prostate cancer.

SUMMARY OF THE INVENTION

Accordingly, the present invention discloses compounds represented by Formula (I):

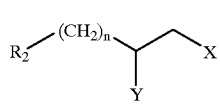

wherein:

n is an integer of 0 to 5;

X is a moiety selected from the group consisting of:

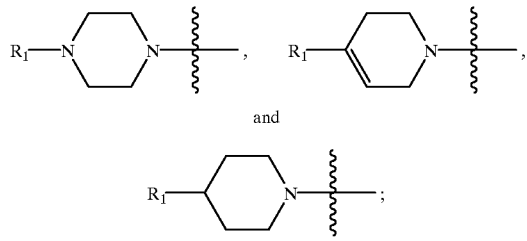

and

Y is a moiety selected from the group consisting of:

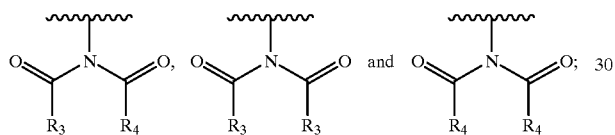

$R^1$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl having 5 or 6 ring atoms containing 1 to 3 heteroatoms which may be the same or different, selected from nitrogen, oxygen and sulfur, optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl having 8 to 20 ring atoms containing 1 to 3 heteroatoms which may be the same or different selected from nitrogen, oxygen and sulfur optionally substituted with 1 to 3 substituents which may be the same or different, selected from alkyl of 1 to 6 carbon atoms, alkoxy of 1 to 6 carbon atoms, —CN, —NO$_2$, and halogen;

$R_2$ is independently H, alkyl of 1 to 6 carbon atoms, cycloalkyl of 3 to 10 carbon atoms, alkenyl of 2 to 10 carbon atoms, alkynyl of 2 to 10 carbon atoms, alkoxy of 1 to 10 carbon atoms, hydroxy, —(CH$_2$)$_z$—O-alkyl of 1 to 6 carbon atoms, —(CH$_2$)$_z$—S-alkyl of 1 to 6 carbon atoms, —(CH$_2$)$_z$OH, perhaloalkyl of 1 to 10 carbon atoms, perhaloalkoxy of 1 to 10 carbon atoms, —CN, —NO$_2$, and halogen; aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl having 5 or 6 ring atoms containing 1 to 3 heteroatoms which may be the same or different, selected from nitrogen, oxygen and sulfur, optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl having 8 to 20 ring atoms containing 1 to 3 heteroatoms which may be the same or different selected from nitrogen, oxygen and sulfur optionally substituted with 1 to 3 substituents which may be the same or different, selected from alkyl of 1 to 6 carbon atoms, alkoxy of 1 to 6 carbon atoms, —CN, —NO$_2$, and halogen;

z is an integer of 1 to 3;

$R_3$ is independently cycloalkyl or cycloalkenyl of 3 to 10 carbon atoms;

$R_4$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; having 5 or 6 ring atoms containing 1 to 3 heteroatoms which may be the same or different, selected from nitrogen, oxygen and sulfur, optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl having 8 to 20 ring atoms containing 1 to 3 heteroatoms which may be the same or different selected from nitrogen, oxygen and sulfur optionally substituted with 1 to 3 substituents which may be the same or different, selected from alkyl of 1 to 6 carbon atoms, alkoxy of 1 to 6 carbon atoms, —CN, —NO$_2$, and halogen;

with the proviso that X is not the radical

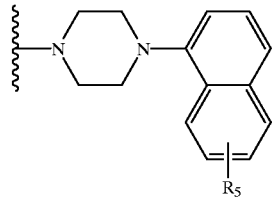

when $R_5$ is H, halogen, alkyl of 1 to 6 carbon atoms, alkoxy of 1 to 6 carbon atoms and hydroxyl; n is 0; $R_2$ is H; Y is the radical

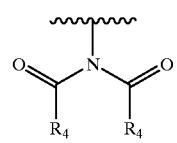

and $R_4$ is phenyl substituted with three substituents which are the same or different selected from H, halogen, alkyl of 1 to 6 carbon atoms and alkoxy of 1 to 6 carbon atoms; or a pharmaceutically acceptable salt thereof.

Among the preferred compounds of Formula (I) of this invention are those in the subgroups, and pharmaceutically acceptable salts thereof:

a) compounds having the general formula:

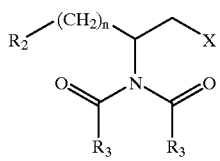

wherein:

R$_2$, R$_3$, X and n are hereinbefore defined;

b) compounds having the general formula:

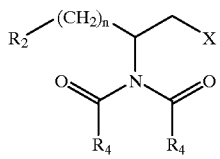

wherein:

R$_2$, R$_4$, X and n are hereinbefore defined;

c) compounds having the general formula:

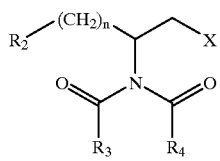

wherein:

R$_2$, R$_3$, R$_4$, X and n are hereinbefore defined;

d) compounds of the general Formula (I)

wherein:

R$_1$ is selected from phenyl optionally substituted with 1 or 2 substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; 2 or 3-furyl, 2 or 3-thienyl, 2-,3- or 4-pyridyl, indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]dioxin; and R$_2$, R$_3$, R$_4$, X and n are hereinbefore defined;

e) compounds of the general Formula (I)

wherein:

R$_2$ is selected from H, alkyl of 1 to 6 carbon atoms, cycloalkyl of 3 to 10 carbon atoms, alkenyl of 2 to 10 carbon atoms, alkynyl of 2 to 10 carbon atoms, alkoxy of 1 to 10 carbon atoms, hydroxy, —(CH$_2$)$_z$—O-alkyl of 1 to 6 carbon atoms, —(CH$_2$)$_z$—S-alkyl of 1 to 6 carbon atoms, —(CH$_2$)$_z$OH, perhaloalkyl of 1 to 10 carbon atoms, perhaloalkoxy of 1 to 10 carbon atoms, —CN, —NO$_2$, and halogen; phenyl optionally substituted with 1 or 2 substituents selected from alkyl of 1 to 6 carbon atoms, cycloalkyl of 1 to 6 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, and perha-loalkoxy of 1 to 10 carbon atoms, —CN, —NO$_2$, and halogen; 2 or 3-furyl, 2 or 3-thienyl, 2-,3- or 4-pyridyl, indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]dioxin; and R$_1$, R$_3$, R$_4$, Y, X, z and n are hereinbefore defined.

Among the more preferred compounds of Formula (I) of this invention are those in the subgroups, and pharmaceutically acceptable salts thereof:

a) compounds having the general formula:

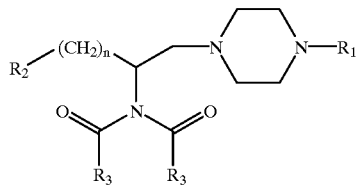

wherein:

R$_1$, R$_2$, R$_3$, and n are hereinbefore defined;

b) compounds having the general formula:

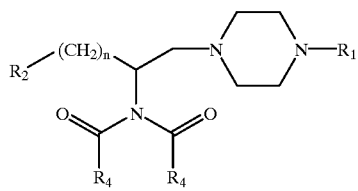

wherein:

R$_1$, R$_2$, R$_4$ and n are hereinbefore defined;

c) compounds having the general formula:

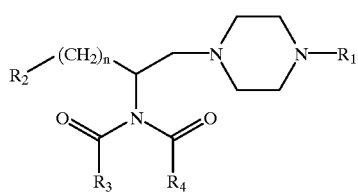

wherein:

R$_1$, R$_2$, R$_3$, R$_4$, and n are hereinbefore defined;

d) compounds having the general formula:

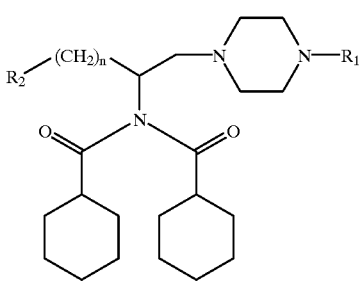

wherein:

R$_1$ is phenyl optionally substituted with one or two substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; indolyl and 2,3-dihydro-benzo[1,4]dioxin; and R$_2$ and n are hereinbefore defined;

e) compounds having the general formula:

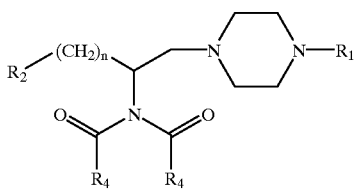

wherein:

R$_1$ is phenyl optionally substituted with one or two substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; indolyl and 2,3-dihydro-benzo[1,4]dioxin;

R$_4$ is phenyl, optionally substituted with one, two or three substituents selected from alkyl of 1 to 6 carbon atoms, cycloallyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; and R$_2$ and n are hereinbefore defined;

f) compounds having the general formula:

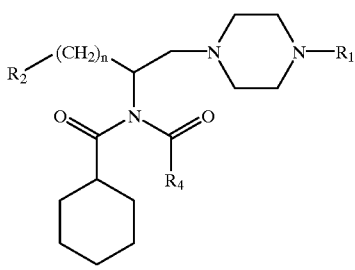

wherein:

R$_1$ is phenyl optionally substituted with one or two substituents selected alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; indolyl and 2,3-dihydro-benzo[1,4]dioxin;

R$_4$ is phenyl, optionally substituted with one, two or three substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; and R$_2$ and n are hereinbefore defined.

Among the most particularly preferred compounds of this invention according to general Formula (I) are the following compounds or pharmaceutically acceptable salts thereof for the method of treating disorders associated with serotonergic neuron-related diseases such as anxiety, depression, eating disorders, high blood pressure, emesis, schizophrenia, the cognitive deficits resulting from neurodegenerative diseases of Alzheimer's Disease and additionally prostate cancer:

Cyclohexanecarboxylic acid cyclohexanecarbonyl-{2-[4-(2-methoxyphenyl)-piperazin-1-yl]-ethyl}-armide dihydrochloride;

Cyclohexanecarboxylic acid cyclohexanecarbonyl-{2-[4-(1H-indol-4-yl)-piperazin-1-yl]-ethyl }-amide dihydrochloride;

Cyclohexanecarboxylic acid cyclohexanecarbonyl-{2-[4-(2,3-dihydro-benzo[1,4]-dioxin)-5-yl}-piperazin-1-yl]-ethyl}-amide sesquihydrochloride monohydrate;

(R)-Cyclohexanecarboxylic acid cyclohexanecarbonyl-{1-methyl-2-[4-(2-methoxyphenyl)-piperazin-1-yl]-ethyl }-amide fumarate;

(R)-Cyclohexanecarboxylic acid cyclohexanecarbonyl-{1-(4-benzyl)-2-[4-(2-methoxy-phenyl)-piperazin-1-yl]-ethyl}-amide fumarate;

(R)-Cyclohexanecarboxylic acid cyclohexanecarbonyl-{1-(4-methoxybenzyl)-2-[4-(2-methoxyphenyl)-piperazin-1-yl]-ethyl}-amide hydrochloride;

(R)-Cyclohexanecarboxylic acid cyclohexanecarbonyl-{1-[4-(2-methoxyphenyl)-piperazin-1-ylmethyl]-2-(1-methyl-1H-indol-3-yl)ethyl}-amide hydrochloride monohydrate;

Cyclohexanecarboxylic acid {2-[4-(2,3-dihydro-benzo[1,4]dioxin-5-yl)-piperazin-1-yl-]ethyl}-amide;

Cyclohexanecarboxylic acid benzoyl-{2-[4-(2,3-dihydro-benzo[1,4]dioxin-5-yl)-piperazin-1-ylethyl]-amide hydrochloride sesquihydrate;

N-Benzoyl-N-{-2-[4-(2-methoxyphenyl)-piperazin-1-yl]-ethyl}-benzamide hydrochloride hemihydrate; and (R)-N-Benzoyl-N-{1-methyl-2-[4-(2-methoxyphenyl)-piperazin-1-yl]-ethyl}-benzamide semifumarate-hemihydrate.

In particular, the present invention also provides a method of treatment of disorders associated with serotonergic neuron-related diseases such as anxiety, depression, eating disorders, high blood pressure, emesis, schizophrenia, the cognitive deficits resulting from neurodegenerative diseases of Alzheimer's Disease and additionally prostate cancer by acting on a 5-HT$_{1A}$ receptor in warm-blooded animals in need thereof, which comprises administering to said warm-blooded animals, preferably mammals, most preferably humans, an effective amount of a compound of Formula (I) or a pharmaceutically acceptable salt thereof.

For the compounds defined above and referred to herein, unless otherwise noted, the following terms are defined.

The term halogen may be selected from fluorine, chlorine, bromine and iodine, unless otherwise specified.

The term alkyl means a branched or unbranched, saturated aliphatic hydrocarbon radical. Examples of alkyl radicals include methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like unless otherwise specified.

The term alkenyl means a branched or unbranched hydrocarbon radical containing at least one carbon-carbon double bond, each double bond being independently cis, trans or a nongeometric isomer.

The term alkynyl means a branched or unbranched hydrocarbon radical containing at least one carbon-carbon triple bond.

The term alkoxy means a branched or unbranched hydrocarbon radical attached through an oxygen bridge and including for example methoxy, ethoxy, n-propoxy, isopropoxy, n-butoxy, t-butoxy and the like.

The term perhaloalkyl means a branched or unbranched hydrocarbon radical in which three of more hydrogens are replaced with halogen and encompass groups such as trifluoromethyl, perfluoroethyl and the like.

The term perhaloalkoxy means a branched or unbranched hydrocarbon radical attached through an oxygen bridge in which three or more hydrogens are replaced with halogen and encompass groups such as trifluoromethoxy, perfluoroethoxy and the like.

The term cycloalkyl means a saturated monocyclic ring which include cyclopropyl, cyclobutyl, cyclopentyl, cyclohexyl, cycloheptyl, cyclooctyl and the like.

The term cycloalkenyl means a unsaturated monocyclic ring containing at least one carbon-carbon double bond, examples which include cyclobutenyl, cyclopentenyl, cyclohexenyl, cycloheptenyl, cyclooctenyl and the like.

Phenyl as used herein refers to a 6-membered aromatic ring.

The term aryl when used alone means a homocyclic aromatic radical, whether or not fused. Preferred aryl groups include phenyl, alpha-naphthyl and beta-naphthyl and the like optionally substituted with one, two or three substituents.

The term heteroaryl means an optionally substituted monocyclic heteroaromatic ring. Preferred are 2- or 3-furyl, 2- or 3-thienyl, or 2-,3- or 4-pyridyl.

The term bicyclic heteroaryl means an optionally substituted bicyclic saturated, unsaturated or aromatic ring system. Preferred are: indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]dioxin.

When $R_3$ and $R_4$ are used multiple times in a moiety such as

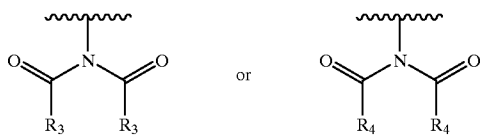

each $R_3$ or $R_4$ may be the same or different.

It is understood by those practicing the art that the definition of compounds of Formula (I) when $R_1$, $R_2$, $R_3$ and $R_4$ contain asymmetric carbons, encompass all possible stereoisomers, mixtures and regioisomers thereof which possess the activity discussed below. Such regioisomers may be obtained pure by standard separation methods known to those skilled in the art. In particular, the definition encompasses any optical isomers and diastereomers as well as the racemic and resolved enantiomerically pure R and S stereoisomers as well as other mixtures of the R and S stereoisomers and pharmaceutically acceptable salts thereof, which possess the activity discussed below. Optical isomers may be obtained in pure form by standard separation techniques or enantiomer specific synthesis. It is understood that this invention encompasses all crystalline forms of compounds of Formula (I). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic and similarly known acceptable acids.

The present invention accordingly provides a pharmaceutical composition which comprises a compound of Formula (I) of this invention in combination or association with a pharmaceutically acceptable carrier. In particular, the present invention provides a pharmaceutical composition which comprises an effective amount of a compound of this invention and a pharmaceutically acceptable carrier.

DESCRIPTION OF THE INVENTION

Compounds Of Formula I are synthesized as described in Scheme I from amine intermediate 1 where n, $R_2$ and X are hereinbefore defined by acylation with two equivalents of acid chloride 2 where $R_3$ is hereinbefore defined to give imide 3, where n, $R_2$, $R_3$ and X are hereinbefore defined, and which is isolated as a pharmaceutically acceptable salt.

Amine intermediate 1 can be further acylated with acid chloride 4 where $R_4$ is hereinbefore defined to give imide 5, where n, $R_2$, $R_4$ and X are hereinbefore defined, and which is isolated as a pharmaceutically acceptable salt.

Scheme I

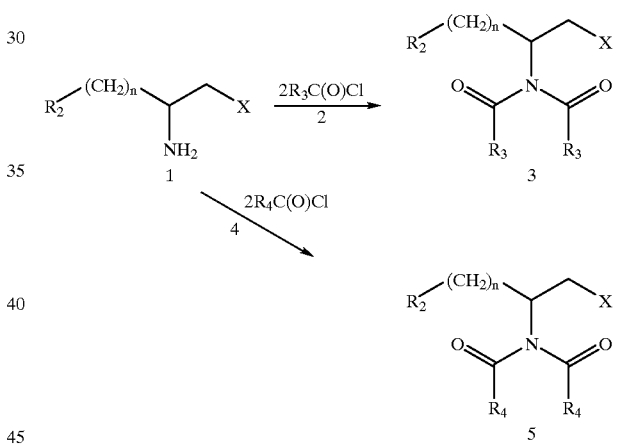

As shown in Scheme II, compounds of Formula I are prepared from amine intermediate 1 where n, $R_2$ and X are hereinbefore defined by sequential acylation using acid chlorides 2 and 4. Acylation of amine intermediate 1 with acid chloride 2 where $R_3$ is hereinbefore defined gives amide 6 where n, $R_2$, $R_3$ and X are hereinbefore defined and which is further acylated with acid chloride 4 to give imide 7, where n, $R_2$, $R_3$, $R_4$ and X are hereinbefore defined and which is isolated as a pharmaceutically acceptable salt.

Scheme II

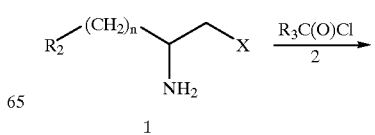

-continued

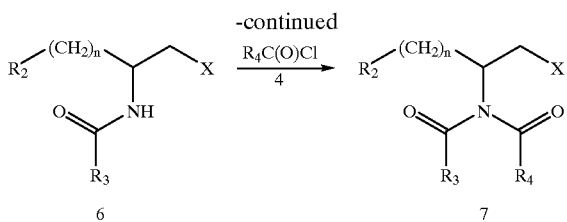

Alternatively, as described in Scheme III, imide 7 may be prepared by introducing the first acyl group using an appropriate carboxylic acid 8 where $R_3$ is hereinbefore defined in the presence of a coupling reagent such as dicyclohexylcarbodiimide (DCC) or alternatively using appropriate coupling reagents which include: 1) N,N'-dicyclohexylcarbodiimide plus 1-hydroxybenzotriazole 2)benzotriazol-1-yloxytris(dimethylamino)phosphonium hexafluorophosphate (BOP-reagent)3) N,N'bis[2-oxo-3-oxazolidinyl]phosphorodiamidic chloride (BOP-Cl)4) diphenylphosphinyl chloride (DPP-Cl)5) diethoxyphosphoryl cyanide 6) 2-chloro-1-methylpyridinium iodide 7) phenyldichlorophosphate plus imidazole to give amide 6 where n, $R_2$, $R_3$ and X are hereinbefore defined. Acylation of amide 6 with acid chloride 4 yields imide 9 where n, $R_2$, $R_3$, $R_4$ and X are hereinbefore defined.

Scheme III

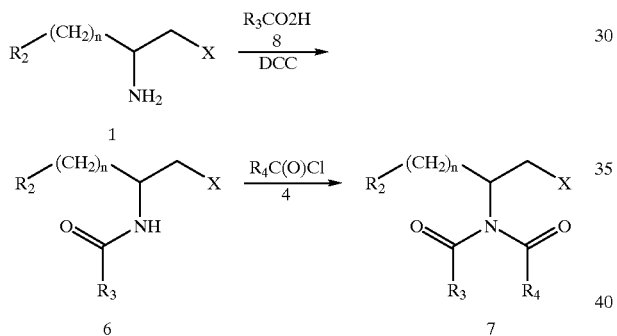

Amine intermediate 1 can be prepared using two general methods. Using the first general method, as shown in Scheme IV, unsubstituted compounds where $R_2$ is H and n is 0 are synthesized from appropriate aryl piperazines, piperidines, or tetrahydropyridines 10, where X is hereinbefore defined by condensation with bromoacetonitrile in the presence of a base which include but are not limited to triethylamine, N,N-diisopropylethylamine or pyridine to give nitrile 11 followed by reduction in the presence of palladium-on-carbon and hydrogen or by methods known to those versed in the art to give amine 1 where $R_2$ is H and n is 0.

Scheme IV

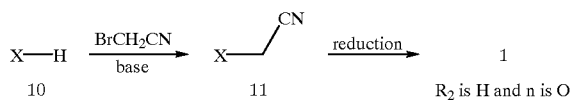

Using the second general method, amine intermediate 1 where $R_2$ and n are hereinbefore defined can be synthesized in three steps as shown in Scheme V. An amino acid 12 where $R_2$ and n are hereinbefore defined is converted to the protected t-butylcarbamate intermediate 13 which is condensed with an appropriate aryl piperazine, piperidine, or tetrahydropyridine 10 in the presence of a coupling reagent (DCC) or alternatively with coupling reagents hereinbefore defined to give protected amine 14. Removal of the t-butlcarbamate (BOC) protecting group under acid catalysis gives amine 15 which is converted, using an appropriate reducing agent such as lithium aluminum hydride or borane to the desired amine intermediate 1 where $R_2$, X and n are hereinbefore defined.

Scheme V

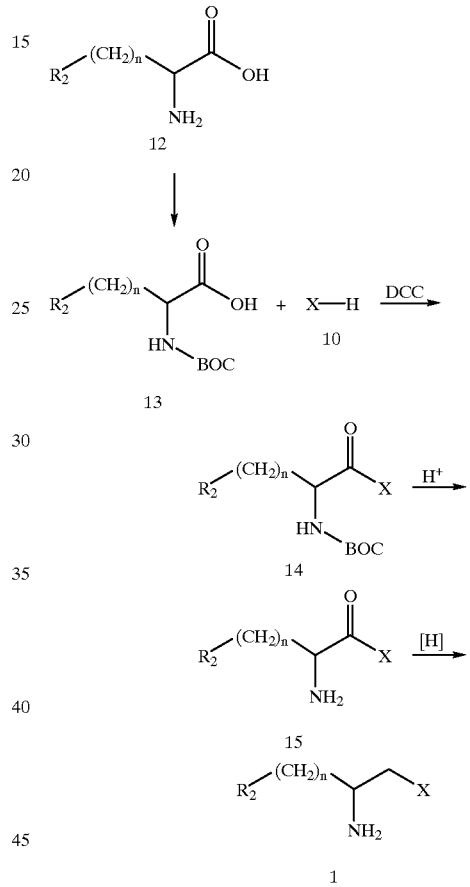

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art. Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

According to a further aspect of the present invention there is provided a series of compounds of Formula (I) or the pharmaceutically acceptable salts thereof as defined herein before for use in a method of treatment of human or animal disease.

The compounds of this invention have high affinity for the 5-$HT_{1A}$ receptor and this activity was established using standard pharmacological test procedures with representative compounds of this invention as follows.

Affinity for the serotonin 5-$HT_{1A}$ receptor was established by assaying the test compound's ability to displace [3H] 8-OHDPAT (dipropylaminotetralin) from its binding site on the receptor complex in CHO cells stably transfected with the human 5-$HT_{1A}$ receptor following a variation of a procedure of J. Zgombick et al., Naunyn-Schmiedeberg's Arch. Pharmacol., 354, 226–236 (1996), as described by J. Dunlop, Y. Zhang, D. L. Smith and L. E. Schechter, Journal of Pharmacological and Toxicological Methods 40, 47–55 (1998). The variation includes: the use of cells containing clonal human 5-$HT_{1A}$ receptor in place of 5-$HT_{1D}$ receptor; the use of [3H]-8-OH-DPAT (1.5 nM) as radioligand in place of [3H]-LSD; nonspecific binding determined with 10 $\mu$M 5-HT; and the test procedure was run at room temperature rather than 37° C. The compounds of this invention displayed high affinity for the 5-$HT_{1A}$ receptor, as described in Table 1.

TABLE 1

| Example | 5-$HT_{1A}$ Affinity ($IC_{50}$) |
| --- | --- |
| Example 6 | 3.10 nM |
| Example 7 | 4.55 nM |
| Example 8 | 4.77 nM |
| Example 9 | 2.69 nM |
| Example 10 | 61.01 nM |
| Example 11 | 0.38 nM |
| Example 12 | 0.78 nM |
| Example 14 | 5.13 nM |
| Example 15 | 23.45 nM |
| Example 16 | 79.60 nM |

Some of the compounds of this invention displayed 5-$HT_{1A}$ partial agonist activity, as assessed by the test compound's ability to stimulate the binding of [35S]-GTP$_\gamma$S to the 5-$HT_{1A}$ receptor-G protein complex in CHO cells stably transfected with the human 5-$HT_{1A}$ receptor following a variation of the procedure described by Lazareno and Birdsall (Br. J. Pharmacol., 109, 1120 (1993). The variation includes: the use of cells containing clonal human 5-$HT_{1A}$ receptor rather than muscarinic receptors; the pH of the medium was 8 rather than 7.4; the use of 10 $\mu$M GDP; and the test procedure was run at 37° C. rather than 30° C. The compounds of this invention which demonstrated agonist activity in this assay possessed $IC_{50}$ values between 1 and 100 nM.

Some of the compounds of this invention demonstrated 5-$HT_{1A}$ antagonist activity, as measured by the test compound's ability to inhibit forskolin-stimulated cAMP turnover in CHO cells stably transfected with the human 5-$HT_{1A}$ receptor using a variation of a procedure of J. Zgombick et al., Naunyn-Schmiedeberg's Arch. Pharmacol., 354, 226–236 (1996), as described by J. Dunlop, Y. Zhang, D. L. Smith and L. E. Schechter, Journal of Pharmacological and Toxicological Methods 40, 47–55 (1998). The variation includes: cAMP formation determined using a Scintillation Proximity Assay (SPA); and centrifugation was unnecessary. The compounds of this invention which demonstrated 5-$HT_{1A}$ antagonist activity in this assay possessed $IC_{50}$ values between 1 and 100 nM.

Based on the activity in the standard pharmacological test procedures, the compounds of this invention modulate serotonergic activity and therefore are useful in the treatment of disorders associated with serotonergic neuron-related diseases such as anxiety, depression, eating disorders, high blood pressure, emesis, schizophrenia, the cognitive deficits resulting from neurodegenerative diseases of Alzheimer's Disease and additionally prostate cancer.

Thus according to this aspect of this invention there is provided the use of compounds of the Formula (I) or the pharmaceutically acceptable salts thereof in the manufacturing of medicament for use in the production of agonists and antagonists useful as pharmaceutical compositions for preventing and treating serotollergic neuron-related diseases such as anxiety, depression, eating disorders, high blood pressure, emesis, schizophrenia, the cognitive deficits resulting from neurodegenerative diseases of Alzheimer's Disease and additionally prostate cancer in a warm-blooded animal such as a human.

The compounds of this invention may be formulated neat or may be combined with one or more pharmaceutically acceptable carriers for administration. For example, solvents, diluents and the like; and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The following examples are presented to illustrate rather than limit the methods for the production of representative compounds of the invention.

EXAMPLE 1

[4-(2,3-Dihydro-benzo[1,4]dioxin-5-yl)-piperazin-1-yl]-acetonitrile

A solution of bromoacetonitrile (2.38 g, 19.86 mmol), benzodioxin-5-ylpiperazine (5.1 g, 19.86 mmol) and triethylamine (11.05 mL, 79.4 mmol) in dimethylformamide (50 mL) was stirred under a nitrogen atmosphere at 70° C. for 3 days. Water (300 mL) was added and the product extracted into ethyl acetate (6×50 mL). The combined organic layers were washed with water (50 mL) and brine (50 mL) and dried over anhydrous sodium sulfate. Filtration and concentration on a rotary evaporator gave the desired compound as a light yellow oil which solidified on standing (5.1 g, 99% yield). The compound was isolated as its hydrochloride salt by treatment in ethyl acetate with ethereal HCl to yield a light yellow solid, mp=193–194° C.; MS (+) ESI m/z=260 (M+H)$^+$.

Analysis for $C_{14}H_{17}N_3O_2$.HCl.0.75 $H_2O$ Calculated: C, 54.37; H, 6.36; N, 13.59. Found: C, 54.55; H, 6.36; N, 15.50.

EXAMPLE 2

2-[4-(2,3-Dihydro-benzo[1,4]dioxinyl-5-yl)-piperazin-1-yl]-ethylamine

A solution of [4-(2,3-dihydro-benzo[1,4]dioxin-5-yl)-piperazin-1-yl]-acetonitrile (1.55 g, 5.97 mmol) in anhydrous tetrahydrofuran (10 mL) at 0° C. under an atmosphere of nitrogen was treated dropwise with a 1M solution of lithium aluminum hydride in tetrahydrofuran (6.0 mL, 6.0 mmol). The resulting solution was stirred overnight during which time it came up to room temperature. The reaction was quenched by dropwise addition of saturated aqueous ammonium chloride just until foaming ceased. The resulting mixture was filtered through a pad of diatomaceous earth, which was washed throughly with ethyl acetate. The combined organic solution was washed with water (25 mL) and brine (25 mL) and dried over anhydrous sodium sulfate. Filtration and concentration gave the title compound as a white solid, mp=68–69° C.; MS (+) ESI m/z=264 (M+H)$^+$.

Analysis for $C_{14}H_{12}N_3O_2$ Calculated: C, 63.85; H, 8.04; N, 15.96. Found: C, 63.64; H, 8.13; N, 15.36.

EXAMPLE 3

(R)-{1-methyl-2-[4-(2-methoxylhenyl)-piperazin-1-yl]-2-oxo-ethyl}-carbamic acid-tert-butyl ester To a solution of D-N-(tert-butoxycarbonyl)-alanine (4.0 g, 21.1 mmol) and 1-(2-methyxophenyl)-piperazine (4.47 g, 23.3 mmol) in dimethylformamide (40 mL) at 0° C. was added 1-(3-dimethylaminopropyl)-3-ethylcarbodiimide hydrochloride (4.05 g, 21.1 mmol), 1-hydroxybenzotriazole hydrate (3.71 g, 27.5 mmol) and 1-methyl morpholine (3.4 mL, 31.7 mmol). The resulting mixture was stirred overnight, during which time it came up to room temperature. The reaction mixture was then diluted with water (100 mL) and ethyl acetate (150 mL) and the layers separated. The aqueous layer was extracted with three additional 30 mL portions of ethyl acetate. The combined organic layers were washed with 1N aqueous HCl (50 mL) and saturated aqueous $NaHCO_3$ and then dried over anhydrous sodium sulfate. Filtration and concentration on a rotary evaporator yielded the crude product which was purified by flash chromatography on silica gel (ethyl acetate/hexane) to afford the desired (R)-{1-methyl-2-[4-(2-methoxyphenyl)-piperazin-1-yl]-2-oxo-ethyl}-carbamic acid-tert-butyl ester (7.24 g, 95%) as a yellow oil.

EXAMPLE 4

(R)-{1-methyl-2-[4-(2-methoxypheniyl)-piperazin-1-yl]-2-amino-propan-2-1-one

The (R)-{1-methyl-2-[4-(2-methoxyphenyl)-piperazin-1-yl]-2-oxo-ethyl}-carbamic acid-tert-butyl ester (7.24 g, 19.9 mmol) was dissolved in a 1:1 mixture of 4N aqueous HCl/dioxane (100 mL) and stirred overnight at room temperature. Concentration of the mixture on a rotary evaporator yielded the required (R)-(1-methyl-2-[4-(2-methoxyphenyl)-piperazin-1-yl]-2-amino-propan-2-1-one (5.90 g, 99%) as a hydrochloride salt.

EXAMPLE 5

(R)-{2-[4-(2-methoxyphenyl)-piperazin-1-yl]-1-methyl-ethyl}-amine

The above mentioned (R)-{1-methyl-2-[4-(2-methoxyphenyl)-piperazin-1-yl]-2-amino-propan-2-1-one hydrochloride (5.90 g, 19.7 mmol) was dissolved in anhydrous tetrahydrofuran (60 mL) at room temperature. Triethylamine (6.3 mL, 45 mmol) was added, followed by dropwise addition of a 1M solution of borane in tetrahydrofuran (77.5 mL, 45 mmol). The resulting mixture was refluxed for 18 hours. After cooling the reaction mixture to room temperature, ethyl acetate (60 mL) and 2N aqueous HCl were added and the resulting mixture was stirred at room temperature for one hour. The layers were separated and the aqueous layer was made basic by careful addition of 50% aqueous NaOH. The resulting basic mixture was extracted with three 50 mL portions of ethyl acetate. The combined organic layers were washed with brine (50 mL) and dried over anhydrous sodium sulfate. Filtration and concentration on a rotary evaporator yielded 4.62 g (94%) of the desired of 2-[4-(2-methoxyphenyl)-piperazin-1-yl]-ethylamine as a colorless oil which was used without further purification.

EXAMPLE 6

Cyclohexanecarboxylic acid cyclohexanecarbonyl-{2-[4-(2-methoxyphenyl)-piperazin-1-yl]-ethyl}-amide dihydrochloride To a solution of 2-[4-(2-methoxyphenyl)-piperazin-1-yl]-ethylamine (0.40 g, 1.7 mmol) and triethylamine (0.95. mL, 6.8 mmol) in dichloromethane (20 mL) at 0° C. was added cyclohexanecarboxylic acid chloride (0.56 g, 3.8 mmol). The reaction mixture was allowed to stir under nitrogen for eighteen hours, during which time the reaction came up to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to its dihydrochloride salt with ethanolic HCl to yield 0.77 g (86%) of the title compound as a white solid; mp=159–160° C.; MS (+) ESI m/z=456 (M+H)$^+$.

Analysis for $C_{27}H_{41}N_3O_2 \cdot 2HCl$ Calculated: C, 61.35; H, 8.20; N, 7.95. Found: C, 61.16; H, 8.29; N, 8.04.

EXAMPLE 7

Cyclohexanecarboxylic acid cyclohexanecarbonyl-{2-[4-(1H-indol-4-yl)-piperazin-1-yl]-ethyl}-amide dihydrochloride To a solution of 2-[4-(1H-indol-4-yl)-piperazin-1-yl]-ethylamine (0.16 g, 0.66 mmol) and triethylamine (0.137 mL, 2.64 mmol) in dichloromethane (10 mL) at 0° C. was added cyclohexanecarboxylic acid (0.22 g, 1.49 mmol). The reaction mixture was allowed to stir under nitrogen for eighteen hours, during which time the reaction came up to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to its dihydrochloride salt with ethanolic HCl to yield 0.22 g (81%) of the title compound as an off-white solid; mp 144–146° C.; MS (+) ESI m/z=465 (M+H)$^+$.

Analysis for $C_{28}H_{40}N_4O_2 \cdot 2HCl$ Calculated: C, 62.56; H, 7.88; N, 10.42. Found: C, 62.32; H, 8.01; N, 10.27.

EXAMPLE 8

Cyclohexanecarboxylic acid cyclohexanecarbonyl-{2-[4-(2,3-dihydro-benzo[1,4]-dioxin)-5-yl}-piperazin-1-yl]-ethyl}-amide sesquihydrochloride monohydrate To a solution of 2-[4-(2,3-dihydro-benzo[1,4]-dioxin)-5-yl}-piperazin-1-yl]-ethylamine (0.20 g, 0.76 mmol) and triethylamine (0.31 mL, 2.28 mmol) in dichloromethane (10 mL) at 0° C. was added cyclohexanecarboxylic acid chloride (0.33 g, 2.28 mmol). The reaction mixture was allowed to stir under nitrogen for eighteen hours, during which time the reaction came up to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (ethyl acetate/hexane) and then converted to its 1.5 hydrochloride monohydrate salt in ethyl acetate to yield 0.28. g (67%) of the title compound as a white solid; mp=148–149° C.; MS (+) ESI m/z=484 (M+H)$^+$.

Analysis for $C_{28}H_{41}N_3O_4 \cdot 1.5 \, HCl \cdot H_2O$ Calculated: C, 60.45; H, 8.06; N, 7.55. Found: C, 60.45; H, 7.92; N, 7.56.

EXAMPLE 9

(R)-Cyclohexanecarboxylic acid cyclohexanecarbonyl-{1-methyl-2-[4-(2-methoxyphenyl)-piperazin-1-yl]-ethyl}-amide fumarate To a solution of (R)-1-methyl-2-[4-(2-methoxyphenyl)-piperazin-1-yl]-ethylamine (0.48 g, 1.9 mmol) and triethylamine (2.0 mL, 14.4 mmol) in dichloromethane (20 mL) at 0° C. was added cyclohexanecarboxylic acid chloride (1.04 g, 7.2 mmol). The reaction mixture was allowed to stir under nitrogen for eighteen hours, during which time the reaction came up to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (ethyl acetate/hexane) and then converted to its monofumarate salt in ethanol to yield 0.87 g (78%) of the title compound as an off-white solid; mp 127–130° C.; MS (+) ESI m/z=470 (M+H)$^+$.

Analysis for $C_{28}H_{43}N_3O_3 \cdot C_4H_4O_4$ Calculated: C, 65.62; H, 8.09; N, 7.17. Found: C, 65.54; H, 8.12; N, 7.07.

EXAMPLE 10

(R)-Cyclohexanecarboxylic acid cyclohexanecarbonyl-{1-benzyl)-2-[4-(2-methoxyphenyl)-piperazin-1-yl]-ethyl}-amide fumarate To a solution of (R)-1-(4-benzyl)-2-[4-(2-methoxyphenyl)-piperazin-1-yl]-ethyl-amine (0.49 g, 1.5 mmol) and triethylamine (0.84 mL, 6.0 mmol) in dichloromethane (10 mL) at 0° C. was added of cyclohexanecarboxylic acid chloride (0.66 g, 4.5 mmol). The reaction mixture was allowed to stir under nitrogen for eighteen hours, during which time the reaction came up to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (ethyl acetate/hexane) and then converted to its fumarate salt in ethyl acetate to yield 0.79 g (80%) of the title compound as an off-white solid; mp=146–147° C.; MS (+) ESI m/z=546 (M+H)$^+$.

Analysis for $C_{34}H_{47}N_3O_3 \cdot C_4H_4O_4$ Calculated: C, 68.96; H, 7.77; N, 6.35. Found: C, 68.62; H, 7.80; N, 6.29.

EXAMPLE 11

(R)-Cyclohexanecarboxylic acid cyclohexanecarbonyl-{1-(4-methoxybenzyl)-2-[4-(2-methoxyphenyl)-piperazin-1-yl]-ethyl}-amide hydrochloride To a solution of (R)-1-(4-methoxybenzyl)-2-[4-(2-methoxyyphenyl)-piperazin-1-yl]-ethylamine (0.21 g, 0.59 mmol) and triethylamine (0.33 mL, 2.36 mmol) in dichloromethane (10 mL) at 0° C. was added cyclohexanecarboxylic acid chloride (0.19 g, 1.33 mmol). The reaction mixture was allowed to stir under nitrogen for eighteen hours, during which time the reaction came up to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (dichloromethane/methanol) and then converted to its dihydrochloride salt with ethanolic HCl to yield 0.30 g (84%) of the title compound as an off-white solid; mp=106–108° C.; MS (+) ESI m/z=576 (M+H)$^+$.

Analysis for $C_{35}H_{49}N_3O_4$.HCl Calculated: C, 68.66; H, 8.23; N, 6.86. Found: C, 68.57; H, 7.87; N, 6.95.

EXAMPLE 12

(R)-Cyclohexanecarboxylic acid cyclohexanecarbonyl-{1-[4-(2-methoxyphenyl)-piperazin-1-ylmethyl]-2-(1-methyl-1H-indol-3-yl) ethyl}-amide hydrochloride monohydrate To a solution of (R)-1-[4-(2-methoxyphenyl)-piperazin-1-ylmethyl]-2-(1-methyl-1H-indol-3-yl)ethylamine (0.21 g, 0. 56 mmol)and triethylamine (0.31 mL, 2.24 mmol) in dichloromethane (10 mL) at 0° C. was added cyclohexanecarboxylic acid chloride (0.18 g, 1.26 mmol). The reaction mixture was allowed to stir under nitrogen for 18 hours, during which time it came up to room temperature. The reaction mixture was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (dichloromethane/methanol) and converted to its hydrochloride.monohydrate salt with ethanolic HCl yield 0.28 g (77%) of the title compound as a white solid; mp=136–138° C.; MS (+) ESI m/z=599 (M+H)$^+$.

Analysis for $C_{37}H_{50}N_4O_3$.HCl.$H_2O$ Calculated: C, 68.02; H, 8.17; N, 8.57. Found: C, 67.29; H, 7.77; N, 8.31.

EXAMPLE 13

Cyclohexanecarboxylic acid {2-[4-(2,3-dihydro-benzo[1,4]dioxin-5-yl)-piperazin-1-yl-]ethyl}-amide A solution of 2-[4-(2,3-dihydro-benzo[1,4]dioxin-5-yl)-piperazin-1-yl-]ethylamine (0.20 g, 0.76 mmol) in dichloromethane (5 mL) was treated with cyclohexanecarbonyl chloride (0.11 g, 0.76 mmol) at 0° C. under a nitrogen atmosphere. The resulting mixture was stirred overnight, during which time it came up to room temperature. The product was precipitated by the addition of hexane to yield the hydrochloride semihydrate salt of the titled compound (0.25 g, 80%) as a white solid; mp=165–166° C.; MS (+) ESI m/z=374 (M+H)$^+$.

Analysis for $C_{21}H_{31}N_3O_3$.HCl.0.5 $H_2O$ Calculated: C, 60.20; H, 7.94; N, 10.03. Found: C, 60.19; H, 7.88; N, 9.83.

EXAMPLE 14

Cyclohexanecarboxylic acid benzoyl-{2-[4-(2,3-dihydro-benzo[1,4]dioxin-5-yl)-piperazin-1-ylethyl]-amide hydrochloride sesquihydrate To a solution of cyclohexanecarboxylic acid {2-[4-(2,3-dihydro-benzo[1,4]dioxin-5-yl)-piperazin-1-yl-]ethyl}-amide hydrochloride semihydrate (0.14 g, 0.34 mmol) and triethylamine (0.14 mL, 1.02 mmol) in dichloromethane (5 mL) at 0° C. was added benzoyl chloride (0.096 g, 0.68 mmol). The reaction mixture was allowed to stir under nitrogen for 18 hours, during which time it came up to room temperature. The reaction mixture was then concentrated on a rotary evaporator, diluted with ethyl acetate and washed with $H_2O$ and brine. The organic phase was dried over anhydrous sodium sulfate, filtered and concentrated on a rotary evaporator to yield the crude product, which was purified by flash chromatography on silica gel (ethyl acetate/hexane) and converted to its hydrochloride.sesquihydrate salt with ethereal HCl to yield 0.08 g (45%) of the title compound as a white solid; mp=169–171° C.; MS (+) ESI m/z=478 (M+H)$^+$.

Analysis for $C_{28}H_{35}N_3O_4$.HCl.1.25 $H_2O$ Calculated: C, 62.68; H, 7.23; N, 7.83. Found: C, 62.27; H, 6.82; N, 7.54.

EXAMPLE 15

N-benzoyl-N-{-2-[4-(2-methoxyphenyl)-piperazin-1-yl]-ethyl}-benzamide hydrochloride hemihydrate To a solution of 2-[4-(2-methoxyphenyl)-piperazin-1-yl]-ethylamine (0.50 g, 2.12 mmol) and triethylamine (1.2 mL, 8.48 mmol) in dichloromethane (20 mL) at 0° C. was added benzoyl chloride (0.75 g, 6.36 mmol). The reaction mixture was allowed to stir under nitrogen for eighteen hours, during which time the reaction came up to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (ethyl acetate/hexane) and then converted to its hydrochloride hemihydrate salt with ethereal HCl to yield 0.38 g (37%) of the title compound as a white solid mp=208–209° C.; MS (+) ESI m/z=444 (M+H)$^+$.

Analysis for $C_{27}H_{29}N_3O_3$.HCl.0.25 $H_2O$ Calculated: C, 66.93; H, 6.35; N, 8.67. Found: C, 66.59; H, 6.45; N, 8.61.

EXAMPLE 16

(R)-N-Benzoyl-N-{1-methyl-2-[4-(2-methoxyphenyl)-piperazin-1-yl]-ethyl}-benzamide semifumarate-hemihydrate To a solution of (R)-1-methyl-2-[4-(2-methoxyphenyl)-piperazin-1-yl]-ethyl-amine (0.57 g, 2.3 mmol) and triethylamine (1.3 mL, 9.1 mmol) in dichloromethane (20 mL) at 0° C. was added benzoyl chloride (0.45 mL, 3.9 mmol). The reaction mixture was allowed to stir under nitrogen for eighteen hours, during which time it came to room temperature. The reaction mixture was then concentrated on a rotary evaporator, diluted with ethyl acetate and washed with sat. aq. $NaHCO_3$ and brine. The organic phase was dried over anhydrous sodium sulfate, filtered and concentrated on a rotary evaporator to yield the crude product, which was purified by flash chromatography on silica gel (ethyl acetate/hexane) and then converted to its semifumarate salt in ethanol to yield 0.29 g (24%) of the title compound as a tan solid; mp=115–120° C.; MS (+) ESI m/z=458 (M+H)$^+$.

Analysis for $C_{28}H_{31}N_3O_3 \cdot 0.5\ C_4H_4O_4 \cdot 0.70\ H_2O$ Calculated: C, 68.21; H, 6.57; N, 7.95. Found: C, 68.29; H, 6.29; N, 7.62.

What is claimed is:

1. A compound having the Formula (I)

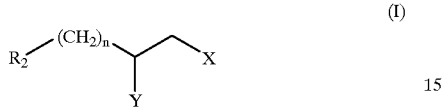

(I)

wherein:

n is an integer of 0 to 5;

X is a moiety

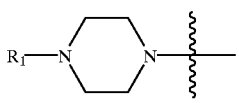

Y is a moiety selected from the group consisting of:

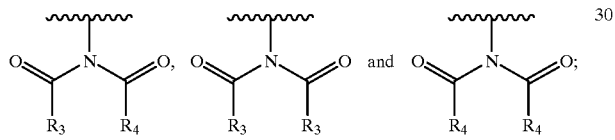

$R_1$ is aryl of 6 to 12 carbon atoms optionally substituted with one or more substituents selected from alkyl of 1 to 6 carbon atoms, cyrloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindoyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

$R_2$ is independently H, alkyl of 1 to 6 carbon atoms, cycloalkyl of 3 to 10 carbon atoms, alkenyl of 2 to 10 carbon atoms, alkynyl of 2 to 10 carbon atoms, alkoxy of 1 to 10 carbon atoms, hydroxy, —(CH$_2$)$_z$—O-alkyl of 1 to 6 carbon atoms, —(CH$_2$)$_z$—S-alkyl of 1 to 6 carbon atoms, —(CH$_2$)$_z$OH, perhaloalkyl of 1 to 10 carbon atoms, perhaloalkoxy of 1 to 10 carbon atoms , —CN, —NO$_2$, and halogen; aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]-dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

z is an integer of 1 to 3;

$R_3$ is independently cycloalkyl or cycloalkenyl of 3 to 10 carbon atoms;

$R_4$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3dihydro-benzo[1,4]-dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

with the proviso that X is not the radical

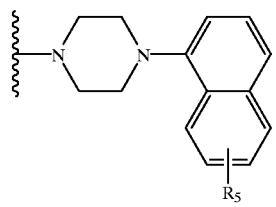

when $R_5$ is H, halogen, alkyl of 1 to 6 carbon atoms, alkoxy of 1 to 6 carbon atoms and hydroxyl; n is 0; $R_2$ is H or alkyl of 1 to 6 carbon atoms; Y is the radical

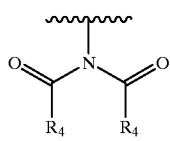

and R₄ is phenyl unsubstituted or substituted with one to three substituents which are the same or different selected from halogen, alkyl of 1 to 6 carbon atoms and alkoxy of 1 to 6 carbon atoms; or a pharmaceutically acceptable salt thereof.

2. A compound according to claim 1 wherein Y is the moiety

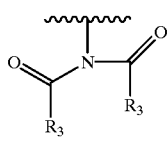

or a pharmaceutically acceptable salt thereof.

3. A compound according to claim 1 wherein Y is the moiety

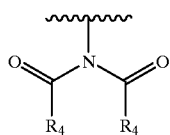

or a pharmaceutically acceptable salt thereof.

4. A compound according to claim 1 wherein Y is the moiety

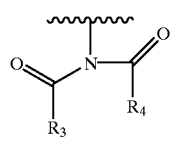

or a pharmaceutically acceptable salt thereof.

5. A compound according to claim 1 wherein:

$R_1$ is phenyl optionally substituted with one or two substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO₂, and halogen; 2 or 3-furyl, 2 or 3-thienyl, 2-,3- or 4-pyridyl; indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiadiazolyl, benzooxazolyl and 2,3-dihydro-benzo[1,4]dioxinyl;

or a pharmaceutically acceptable salt thereof.

6. A compound according to claim 1 wherein:

$R_2$ is selected from H, alkyl of 1 to 6 carbon atoms, cycloalkyl of 3 to 10 carbon atoms, alkenyl of 2 to 10 carbon atoms, alkynyl of 2 to 10 carbon atoms, alkoxy of 1 to 10 carbon atoms, hydroxy, —(CH₂)_z—O-alkyl of 1 to 6 carbon atoms, —(CH₂)_z—S-alkyl of 1 to 6 carbon atoms, —(CH₂)_zOH, perhaloalkyl of 1 to 10 carbon atoms, perhaloalkoxy of 1 to 10 carbon atoms, —CN, —NO₂, and halogen; phenyl optionally substituted with 1 or 2 substituents selected from alkyl of 1 to 6 carbon atoms, cycloalkyl of 1 to 6 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO₂, and halogen; 2 or 3-furyl, 2 or 3-thienyl, 2-,3- or 4-pyridyl; indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]dioxinyl;

or a pharmaceutically acceptable salt thereof.

7. A compound according to claim 1 wherein X is the moiety

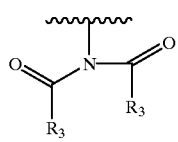

Y is the moiety

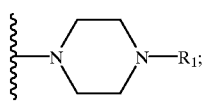

or a pharmaceutically acceptable salt thereof.

8. A compound according to claim 1 wherein X is the moiety

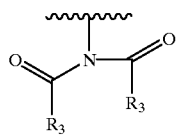

Y is the moiety

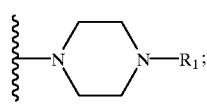

or a pharmaceutically acceptable salt thereof.

9. A compound according to claim 1 wherein X is the moiety

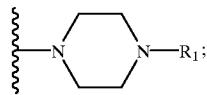

Y is the moiety

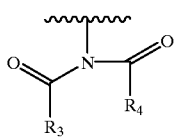

or a pharmaceutically acceptable salt thereof.

10. A compound according to claim 1 wherein X is the moiety

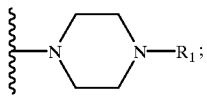

Y is the moiety

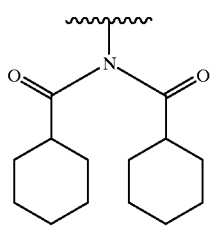

$R_1$ is phenyl optionally substituted with one or two substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; indolyl and 2,3-dihydro-benzo[1,4]dioxinyl;

or a pharmaceutically acceptable salt thereof.

11. A compound according to claim 1 wherein X is the moiety

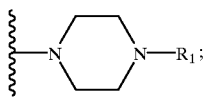

Y is the moiety

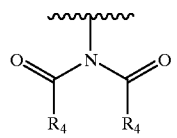

$R_1$ is phenyl optionally substituted with one or two substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; indolyl and 2,3-dihydro-benzo[1,4]dioxinyl;

$R_4$ is phenyl, optionally substituted with one, two or three substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen;

or a pharmaceutically acceptable salt thereof.

12. A compound according to claim 1 wherein X is the moiety

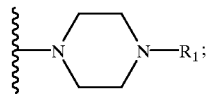

$R_1$ is phenyl optionally substituted with one or two substituents selected alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; indolyl and 2,3-dihydro-benzo[1,4]dioxinyl;

$R_4$ is phenyl, optionally substituted with one, two or three substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen;

Y is the moiety

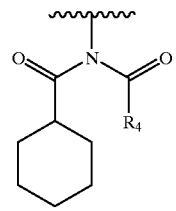

or a pharmaceutically acceptable salt thereof.

13. The compound of claim 1 which is selected from the group consisting of cyclohexanecarboxylic acid cyclohexanecarbonyl-{2-[4-(2-methoxyphenyl)-piperazin-1-yl]-ethyl}-amide dihydrochloride, cyclohexanecarboxylic acid cyclohexanecarbonyl-{2-[4-(1H-indol-4-yl)-piperazin-1-yl]-ethyl}-amide dihydrochloride, cyclohexanecarboxylic acid cyclohexanecarbonyl-{2-[4-(2,3-dihydrobenzo[1,4]-dioxin)-5-yl}-piperazin-1-yl]-ethyl}-amide sesquihydrochloride monohydrate,(R)-cyclohexanecarboxylic acid cyclohexanecarbonyl-{1-methyl-2-[4-(2-methoxyphenyl)-piperazin-1-yl]-ethyl}-amide fumarate,(R)-cyclohexanecarboxylic acid cyclohexanecarbonyl-{1-(4-benzyl)-2-[4-(2-methoxyphenyl)-piperazin-1-yl]-ethyl}-amide fumarate, (R)-cyclohexanecarboxylic acid cyclohexanecarbonyl-{1-(4-methoxybenzyl)-2-[4-(2-methoxyphenyl)-piperazin-1-yl]-ethyl}-amide hydrochloride, (R)-cyclohexanecarboxylic acid cyclohexanecarbonyl-{1-[4-(2-methoxyphenyl)-piperazin-1-ylmethyl]-2-(1-methyl-1H-indol-3-yl)ethyl}-amide hydrochloride monohydrate,cyclohexanecarboxylic acid {2-[4-(2,3-dihydro-benzo[1,4]dioxin-5-yl)-piperazin-1-yl-ethyl}-amide,cyclohexanecarboxylic acid benzoyl-{2-[4-(2,3-dihydro-benzo[1,4]dioxin-5-yl)-piperazin-1-ylethyl]- amide hydrochloride sesquihydrate, N-benzoyl-N-{-2-[4-(2-methoxyphenyl)-piperazin-1-yl]-ethyl}-benzamide hydrochloride hemihydrate, and (R)-N-benzoyl-N-(1-methyl-2-[4-(2-methoxyphenyl)-piperazin-1-yl]-ethyl}-benzamide semifumarate-hemihydrate;

or a pharmaceutically acceptable salt thereof.

14. A pharmaceutical composition comprising an effective amount of a compound of Formula (I)

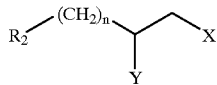

(I)

wherein:

n is an integer of 0 to 5;

X is a moiety

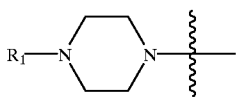

Y is a moiety selected from the group consisting of:

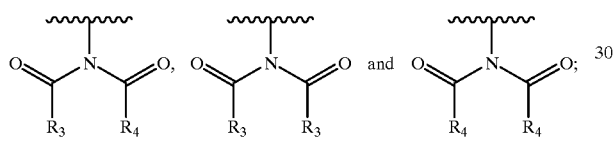

$R_1$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

$R_2$ is independently H, alkyl of 1 to 6 carbon atoms, cycloalkyl of 3 to 10 carbon atoms, alkenyl of 2 to 10 carbon atoms, alkynyl of 2 to 10 carbon atoms, alkoxy of 1 to 10 carbon atoms, hydroxy, —(CH$_2$)$_z$—O-alkyl of 1 to 6 carbon atoms, —(CH$_2$)$_z$—S-alkyl of 1 to 6 carbon atoms, —(CH$_2$)$_z$OH, perhaloalkyl of 1 to 10 carbon atoms, perhaloalkoxy of 1 to 10 carbon atoms, —CN, —NO$_2$, and halogen; aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3dihydro-benzo[1,4]-dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

z is an integer of 1 to 3;

$R_3$ is independently cycloalkyl or cycloalkenyl of 3 to 10 carbon atoms;

$R_4$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]-dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

with the proviso that X is not the radical

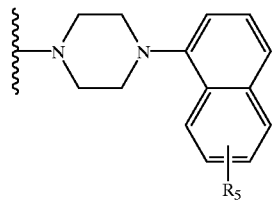

when $R_5$ is H, halogen, alkyl of 1 to 6 carbon atoms, alkoxy of 1 to 6 carbon atoms and hydroxyl; n is 0; $R_2$ is H or alkyl of 1 to 6 carbon atoms; Y is the radical

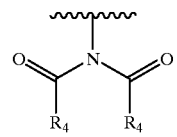

and $R_4$ is phenyl unsubstituted or substituted with one to three substituents which are the same or different selected from halogen, alkyl of 1 to 6 carbon atoms and alkoxy of 1 to 6 carbon atoms; or a pharmaceutically acceptable salt thereof together with one or more pharmaceutically acceptable carriers.

15. A method of treating anxiety in a warm-blooded animal in need thereof, which comprises administering to said warm-blooded animal an effective amount of a compound of Formula (I)

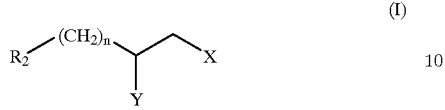

wherein:
n is an integer of 0 to 5;
X is a moiety

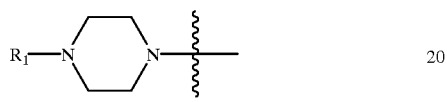

Y is a moiety selected from the group consisting of:

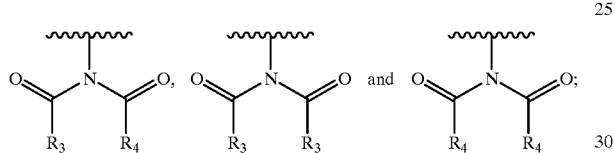

$R_1$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyrddyl, 3pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, qutinolinyl, isoqulnolinyl, benzodioxanyl, benzopyranyl, benzofuranyl, dihydrobenzoturanyl, benzothlophenyl, benzothiazolyl, benzothiadiazolyl, benzooxazolyl and 2,3-dihydro-benzo[1,4]dioxinyl; optionally substituted with 1 to 3 substituents which may be the same or different, selected from alkyl of 1 to 6 carbon atoms, alkoxy of 1 to 6 carbon atoms, —CN, —N$_2$, and halogen;

$R_2$ is independently H, alkyl of 1 to 6 carbon atoms, cycloalkyl of 3 to 10 carbon atoms, alkenyl of 2 to 10 carbon atoms, alkynyl of 2 to 10 carbon atoms, alkoxy of 1 to 10 carbon atoms, hydroxy, —(CH$_2$)$_z$—O-alkyl of 1 to 6 carbon atoms, —(CH$_2$)$_z$—S-alkyl of 1 to 6 carbon atoms, —(CH$_2$)$_z$OH, perhaloalkyl of 1 to 10 carbon atoms, perhaloalkoxy of 1 to 10 carbon atoms, —CN, —NO$_2$, and halogen; aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]-dioxinyl; optionally substituted with 1 to 3 substituents which may be the same or different, selected from alkyl of 1 to 6 carbon atoms, alkoxy of 1 to 6 carbon atoms, —CN, —NO$_2$ and halogen;

z is an integer of 1 to 3;
$R_3$ independently cycloalkyl or cycloalkenyl of 3 to 10 carbon atoms;
$R_4$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen, heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]-dioxinyl; optionally substituted with 1 to 3 substituents which may be the same or different. selected from alkyl of 1 to 6 carbon atoms, alkoxy of 1 to 6 carbon atoms, —CN, —NO$_2$, and halogen;

with the proviso that X is not the radical

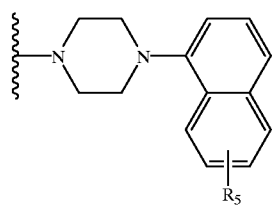

when $R_5$ is H, halogen, alkyl of 1 to 6 carbon atoms, alkoxy of 1 to 6 carbon atoms and hydroxyl; n is 0; $R_2$ is H or alkyl of 1 to 6 carbon atoms; Y is the radical

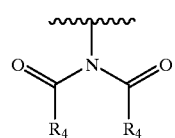

and $R_4$ is phenyl unsubstituted or substituted with one to three substituents which are the same or different selected from halogen, alkyl of 1 to 6 carbon atoms and alkoxy of 1 to 6 carbon atoms; or a pharmaceutically acceptable salt thereof.

16. A method of treating depression in a warm-blooded animal in need thereof, which comprises administering to said warm-blooded animal an effective amount of a compound of Formula (I)

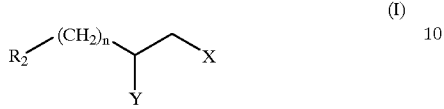

wherein:

n is an integer of 0 to 5;

X is a moiety

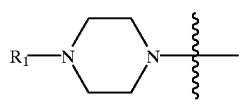

Y is a moiety selected from the group consisting of:

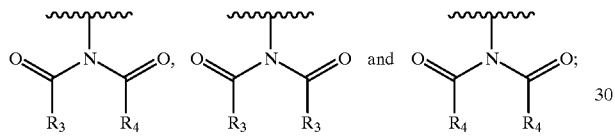

$R_1$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]dioxinyl; optionally substituted with 1 to 3 substituents which may be the same or different selected from alkyl of 1 to 6 carbon atoms, alkoxy of 1 to 6 carbon atoms, —CN, —NO$_2$, and halogen;

$R_2$ is independently H, alkyl of 1 to 6 carbon atoms, cycloalkyl of 3 to 10 carbon atoms, alkenyl of 2 to 10 carbon atoms, alkynyl of 2 to 10 carbon atoms, alkoxy of 1 to 10 carbon atoms, hydroxy, —(CH$_2$)$_z$—O-alkyl of 1 to 6 carbon atoms, —(CH$_2$)$_z$—S-alkyl of 1 to 6 carbon atoms, —(CH$_2$)$_z$OH, perhaloalkyl of 1 to 10 carbon atoms, perhaloalkoxy of 1 to 10 carbon atoms, —CN, —NO$_2$, and halogen; aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; teteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoquinolinyl, benzodioxanyl, benzopyranyl, benzofuranyl, dihydrobenzofuranyl, benzothiophenyl, benzothiazolyl, benzothiadiazolyl, benzooxazolyl and 2,3-dihydrobenzo[1,4]-dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

z is an integer of 1 to 3, $R_3$ is independently cycloalkyl or cycloalkenyl of 3 to 10 carbon atoms;

$R_4$ is aryl of 6 to 12 carbon atoms optionally substituted with one or more substituents selected from alkyl of 1 to 6 carbon atoms, cycloalkyl of 3 to 10 carbon atoms, alkenyl of 2 to 10 carbon atoms, alkynyl of 2 to 10 carbon atoms, hydroxy, alkoxy of 1 to 10 carbon atoms, perhaloalkyl of 1 to 10 carbon atoms, perhaloalkoxy of 1 to 10 carbon atoms, —CN, —NO$_2$, and halogen; heteroaryl selected from 2-furyl, 3-furyl, 2-thienyl, 3-thienyl, 2-pyridyl, 3-pyridyl and 4-pyridyl; optionally substituted with 1 to 3 substituents which may be the same or different selected from alkyl of 1 to 6 carbon atoms, alkoxy of 1 to 6 carbon atoms, —CN, —NO$_2$, and halogen; bicyclic heteroaryl selected from indolyl, azaindolyl, benzimidazolyl, indazolyl, quinolinyl, isoqulnolinyl, benzodioxanyl, benzopyranyl, benzofuranyl, dihydrobenzofuranyl, benzothiophenyl, benzothiazolyl, benzothiadiazolyl, benzooxazolyl and 2,3-dihydro-benzo[1,4]-dioxinyl; optionally substituted with 1 to 3 substituents which may be the same or different, selected from alkyl of 1 to 6 carbon atoms, alkoxy of 1 to 6 carbon atoms, —CN, —NO$_2$, and halogen;

with the proviso that X is not the radical

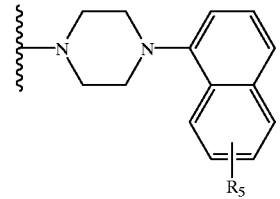

when $R_5$ is H, halogen, alkyl of 1 to 6 carbon atoms, alkoxy of 1 to 6 carbon atoms and hydroxyl; n is 0; $R_2$ is H or alkyl of 1 to 6 carbon atoms; Y is the radical

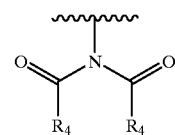

and $R_4$ is phenyl unsubstituted or substituted with one to three substituents which are the same or different selected from halogen, alkyl of 1 to 6 carbon atoms and alkoxy of 1 to 6 carbon atoms; or a pharmaceutically acceptable salt thereof.

17. The method of claim 16 wherein the warm-blooded animal is a human.

18. The method of claim 15 wherein the warm blooded animal is a human.

* * * * *